United States Patent [19]

Roper

[11] 4,414,404
[45] Nov. 8, 1983

[54] PROCESS FOR PRODUCING N-ACYL-D,L-PHENYLALANINE ESTER

[75] Inventor: Jerry M. Roper, Baton Rouge, La.

[73] Assignee: Ethyl Corporation, Richmond, Va.

[21] Appl. No.: 357,232

[22] Filed: Mar. 11, 1982

[51] Int. Cl.³ .......................................... C07C 101/08
[52] U.S. Cl. ...................................... 560/41; 548/228
[58] Field of Search .......................................... 560/41

[56] References Cited

U.S. PATENT DOCUMENTS 3,963,573  6/1976  Stauffer ................................. 195/29
4,262,092  4/1981  Bauer .................................. 435/280

FOREIGN PATENT DOCUMENTS 855051  11/1977  Belgium .

OTHER PUBLICATIONS

Kaneko et al, Synthetic Production and Utilization of Amino Acids, (1974), 171–179.
Bacillus subtilis, Guntelberg Trav. Lab. Carlsberg, Ser. Chim., vol. 29, (1954), 36–48.
Barel, Jour. Biological Chemistry, vol. 23, No. 7, (1968), 1344–1348.
Badshah et al., Jour. Organic Chemistry, vol. 37, No. 18, (1972), 2916–2918.
Knowles et al, Homogeneous Catalysis, vol. 2, 274–282.

Primary Examiner—Bernard Helfin
Attorney, Agent, or Firm—Donald L. Johnson; John F. Sieberth; Patricia J. Hogan

[57] ABSTRACT

A process for preparing a racemic mixture of N-acyl-D,L-phenylalanine ester by reacting the azlactone of N-acyl-acetaminocinnamic acid with hydrogen at a hydrogen pressure of at least about 100 psig at a temperature within the approximate range of about 50°–200° C. in the presence of a nickel hydrogenation catalyst, a lower alkanol and an alkali metal or an alkaline earth metal alkoxide.

13 Claims, No Drawings

PROCESS FOR PRODUCING N-ACYL-D,L-PHENYLALANINE ESTER

BACKGROUND

This invention relates to a process for producing a racemic mixture of N-acyl-D,L-phenylalanine esters. More particularly, this invention provides an especially effective process for obtaining a racemic mixture of N—$C_{1-9}$ acyl-D,L-phenylalanine ester which can be subsequently converted to both L-phenylalanine and D-phenylalanine by treatment with microbially derived serine proteinases.

Until recently, the resolution of racemic D,L-phenylalanine mixtures has followed three different routes of optical resolution in order to obtain one of the optically active antipodes. The first includes asymmetric hydrolysis of N-chloroacetyl-D,L-phenylalanine by the carboxypeptidase in pancrease. A second involves asymmetric hydrolysis of N-acetyl-D,L-phenylalanine by mold aminoacylase which process can be operated in a continuous fashion using a packed column. And, finally, a physico-chemical resolution based on preferential crystallization of isomers from supersaturated solution of acetyl-D,L-phenylalanine ammonium salt. In addition, there are several synthetic methods for production of L-phenylalanine. For example, conversion of L-tyrosine, treatment of synthetic phenylpyruvic acid with transaminase and enzymatic isomerization of synthetic D,L-phenylalanine by microorganisms. Kaneko et al, *Synthetic Production and Utilization of Amino Acids*, J. Wiley & Sons, pp. 171–179 (1974).

In Belgian Patent 855,051, there is taught a method and a composition for treatment of D,L-amino acids to resolve the racemic mixture and obtain L-isomer in which a supported aminoacylase is used to treat aqueous solutions of the D,L-amino acid. The support is a porous inorganic substrate of specified grain size, surface area, pore diameter and volume and is coated with a network polymer film, or carries a tertiary amine or quaternary ammonium salt group. Typical supports are titania, alumina or silica. The network polymer can be polyamino epoxides, polyamine-formaldehyde, phenol-formaldehyde mixtures and polymerized mixtures of vinyl monomers. The aminoacylases are enzymes of animal origin, such as pork kidney extracts or microorganism products, such as from Aspergillus, *Lactobacillus arabinosus, Micrococcus glutamicus*, and *Pseudomonoas cruciviae*. The process includes contacting the amino acids, such as N-acetyl-D,L-amino acid, with the complex of support/tertiary amine/polymer network/enzyme, for example, by passing through a packed column.

In U.S. Pat. No. 3,963,573, there is taught a process for producing optically pure N-acyl-L-methionine by subjecting an N-acyl-D,L-methionine ester to the action of a proteolytic enzyme selected from the group consisting of sulfhydryl proteinases and microbially derived serine proteinases and separating the resulting N-acyl-L-methionine. The art has recognized that certain proteolytic enzymes can be produced in a pure form, such as from *Bacillus subtilis*, Guntelberg Trav. Lab. Carlsberg, Ser. Chim. Vol. 29, p. 36 (1954). The proteolytic enzyme prepared from the strain of *Bacillus subtilis* was purified by crystallization and its physico-chemical properties were determined. The enzymatic properties were investigated insofar as optimum pH for milk coagulation, stability, degradation of casein, hydrolysis of hemoglobin, activators and inhibitors for the enzymes, the effect on ovalbumin and other characteristics. In the *Journal of Biological Chemistry*, Vol. 243, No. 7, pp. 1344–1348 (1968), Barel, examined the activity of Carlsberg and Novo subtilisins toward a number of N-acetylamino acid esters and amino acid esters. The enzymes were also compared with respect to their efficiency in catalyzing aminolysis reactions, their rates of inactivation by certain aromatic sulfonyl halides and the rates of deacylation of their N-trans-cinnamoyl derivatives. Although the enzymes were found qualitatively indistinguishable from the standpoint of substrate specificity, significant quantitative differences were observed. Thus, the microbially derived serine proteinases, for example, Novo and Carlsberg subtilisins exhibited varying of degrees of esterase activity on various N-acyl-L-amino acid esters.

In U.S. Pat. No. 4,262,092, incorporated herein by reference, there is disclosed a process for resolution of N-acyl-D,L-phenylalanine esters employing the activity of serine proteinases. According to the disclosure, optically pure N-acyl-D-phenylalanine ester is produced by reacting a racemic mixture of N-acyl-D,L-phenylalanine ester with a proteolytic enzyme and separating the resulting N-acyl-D-phenylalanine ester from the solution with subsequent removal of the N-acyl and ester groups to provide D-phenylalanine.

Subjecting N-acyl-D,L-phenylalanine ester to the action of such a proteinase provides a mixture of N-acyl-D-phenylalanine ester and N-acyl-L-phenylalanine. The N-acyl-L-phenylalanine can be readily separated from the mixture by conventional means, for example, by adjusting the pH of an aqueous mixture thereof and extracting with an organic solvent such as chloroform, ethyl acetate, butyl acetate, methylene chloride and the like. The isolated N-acyl-L-phenylalanine can then be hydrolyzed to yield L-phenylalanine. The N-acyl-D-phenylalanine ester can be converted to D-phenylalanine by known simple hydrolysis procedures such as dissolving the ester in 2 N HBr and heating for a time at 80°–100° C. The preparation of amino acids by subjecting a racemic mixture of N-acyl-D-phenylalanine ester and N-acyl-L-phenylalanine ester to the action of a proteolytic enzyme provides the economic benefits of producing high purity material in high yields at a rapid rate while using a readily available and inexpensive material, such as enzyme. Accordingly, if a simple one-step method were available for producing a racemic mixture of N-acyl-D,L-phenylalanine esters which could be inexpensively treated with proteolytic enzyme in accordance with the foregoing procedure to produce both L-phenylalanine and D-phenylalanine, the overall process would provide an even more attractive route to phenylalanine.

In accordance with the present invention, such a process now has been discovered and involves the catalytic hydrogenation of the azlactone of N-acyl-acetaminocinnamic acid over a nickel hydrogenation catalyst to produce a racemic mixture of N-acyl-D,L-phenylalanine ester.

While there are several methods available for converting azlactones to the corresponding acylamino acids or amino acids, no process has been disclosed or is available insofar as the Applicant is aware for converting an azlactone to a racemic mixture of N-acyl-D,L-phenylalanine ester. For example, in the *Journal of Organic Chemistry*, Vol. 37, No. 18, pp. 2916–2918 (1972), Badshah, Khan and Kidwai report that there are three general methods, employing reduction and hydrolysis, for the conversion of azlactones to the corresponding acylamino acids or amino acids. Reduction can be effected with sodium or sodium amalgam in water or ethanol, with hydriodic acid and red phosphorus in acetic acid or acetic anhydride, or catalytically over platinum or palladium in the presence of hydrogen. Though most amino acids, excepting tryptophane, have been synthesized by treatment with hydriodic acid and red phosphorus, the method using sodium or amalgam is not of wide applicability. Catalytic reduction has been less favored owing to the high cost of platinum and palladium which becomes a factor in large scale laboratory preparations and resistance of azlactones to hydrogenation which requires their initial hydrolysis to the unsaturated acylamino acids. In an attempt to improve upon the catalytic hydrogenation method for preparing amino acids, Badshah, Khan and Kidwai devised a method for preparing amino acids from azlactones utilizing a reductive hydrogenation of a suspension of azlactone in alcoholic ammonia of Raney nickel at elevated hydrogenation pressure and room temperature. The resulting acylamino acid amide is then hydrolyzed either to acylamino acid or to the desired amino acid by mild or stringent treatment with acid or alkali.

In *Homogeneous Catalysis*, Vol. 2, pp. 274–282, Knowles, Sabacky and Vineyard report the preparation of α-amino acids by an asymmetric hydrogenation of azlactone using a rhodiumchiral phosphine catalyst.

SUMMARY

Thus, in one aspect of the invention, there is provided a process for producing a racemic mixture of N-acyl-D,L-phenylalanine ester which comprises reacting the azlactone of N-acyl-acetaminocinnamic acid with hydrogen at a hydrogen pressure of at least about 100 psig at a temperature within the approximate range of about 50°–200° C. in the presence of a nickel hydrogenation catalyst, a lower alkanol and an alkali metal or alkaline earth metal alkoxide.

A variety of specific azlactones of N-acyl-acetaminocinnamic acid starting material can be used in the invention. Preferably, the acyl group is derived from fatty acids containing 1–9 carbon atoms. More particularly, the N-acyl group will preferably be formyl, acetyl, propionoyl, butyroyl, valeroyl, caproyl, enathoyl, capryryl or pelargonoyl. Especially suitable examples of acyl groups are formyl, acetyl and propionoyl. A most preferred starting reactant is the azlactone of N-acetyl-acetaminocinnamic acid.

The ester group in the N-acyl-D,L-phenylalanine ester mixture can be derived from a variety of alcohols containing from 1 to about 10, preferably from 1–6, carbon atoms. Especially suitable examples of ester groups are methyl, ethyl, n-propyl, isopropyl, n-butyl, sec. butyl, and isobutyl.

Azlactones of N-acylacetaminocinnamic acid can be prepared by methods well known in the art such as, for example, by heating a mixture of glycine, benzaldehyde, acetic anhydride, and anhydrous sodium acetate (Herbst and Shemin, *Organic Synthesis*, Coll. Vol. II, J. Wiley & Sons, p. 3, 1943).

In general, the catalytic hydrogenation is conducted at elevated pressures and at elevated temperatures in the presence of a hydrogenation catalyst. Pressures of about 100–1000 psig are suitable. Higher pressures may be used, but the improvement in operation at such higher pressures usually does not warrant the added manipulative difficulties encountered at such pressures.

Temperatures are preferably held within the range of about 50°–200° C. and within this range, 60°–100° C. is most desirable.

The reaction is carried out in the presence of an active nickel hydrogenation catalyst. This may be any of a wide variety of commercially available nickel catalysts, typical of which are pyrophoric catalysts such as Raney nickel and similar catalysts. Other suitable hydrogenation catalysts which may be used are those made by the reduction of nickel salts and oxides, such as nitrates, formates, carbonates, oxides and the like. These reduced nickel catalysts are frequently deposited on inert carriers such as various earths, kieselghur, alumina and the like.

The concentration of nickel hydrogenation catalyst may be varied over a wide range, depending on the particular activity of the catalyst being used. Raney nickel is the most preferred catalyst. Preferably, the ratio of catalyst to azlactone should be in the range of from about 3–100 grams of catalyst to one mole of azlactone. Higher amounts of catalyst per mole of azlactone may be used, if desired, although there is no particular advantage to using such a high ratio and the added manipulations and expense required make such high ratios undesirable.

In the reduction, a considerable excess of hydrogen should be present to force the reaction to completion and to increase its velocity. The particular concentration of hydrogen is not important except that a large excess should be used.

The reaction is typically completed within 2 to 5 hours.

The reaction is most advantageously carried out by forming a slurry of azlactone in alkanol at room temperature and thereafter adding the alkoxide reactant to the slurry with stirring. The hydrogenation catalyst is then added to the resultant solution and the mixture is placed in a sealed hydrogenation vessel where the mixture is hydrogenated at elevated pressure and temperature until the reaction goes to completion. The reaction mixture is then cooled, removed from the vessel, filtered to remove the catalyst, concentrated and the N-acyl-D,L-phenylalanine ester recovered by conventional extraction procedures.

Typically, from about 2 to 40 moles of alcohol reactant per mole of azlactone is used in the process of the invention with a large excess of alcohol being highly desirable since the alcohol component serves both as reactant and reaction solvent in the process.

The alkoxide component of the process is an alkaline metal or alkaline earth metal alkoxide reactant having up to 10 carbon atoms in the molecule. Sodium, potassium, rubidium, magnesium, barium and calcium alkali and alkaline earth metals are suitable for use in the present process. An especially preferred alkoxide suitable or use in the present process is sodium methoxide. The alkoxide reactant is present in the reaction in amounts ranging from about 0.01 to 1 mole of alkoxide per mole of azlactone.

The following examples will serve to illustrate specific embodiments of the present invention.

EXAMPLE 1

Preparation of N-Acetyl-Acetaminocinnamic Acid

Glycine (37.5 g, 0.5 mol) and anhydrous sodium acetate (30 g, 0.37 mol) were slurried in a mixture of benzaldehyde (79 g, 0.74 mol) and acetic anhydride (283 ml, 3 mol). The mixture was warmed until dissolution was complete; then refluxed for one hour. Upon cooling, the back reaction mixture afforded yellow crystals, which were collected, washed with cold water, and dried in vacuo over phosphorus pentoxide to yield 62 g (67%) of the azlactone of N-acetyl-acetaminocinnamic acid. The melting point was 147°-148° C. The proton NMR agreed with the conclusion that the azlactone of N-acetyl-acetaminocinnamic acid was prepared.

EXAMPLE 2

Preparation of N-Acetly-D,L-Phenylalanine Methyl Ester

A methanol (24 ml) slurry of the azlactone of N-acetyl-acetaminocinnamic acid (18.7 g, 0.10 mol) was treated with sodium methoxide (0.54 g. 0.01 mol) and the resulting dark solution was stirred for 10 minutes. The solution was then hydrogenated (200 psi hydrogen) over Raney nickel (5.87 g, 0.10 mol) in a sealed Parr autoclave at 50° C. for 2.5 hours. After cooling the reaction mixture was filtered through a Celite pad to remove the nickel, and concentrated in vacuo to afford a red oil which was slurried in diethyl ether (200 ml). The ethereal slurry was shaken with cold hydrochloric acid (0.5N, 100 ml) for approximately one minute. The layers were separated and the aqueous portion was extracted with additional diethyl ether (100 ml). The combined ether extract was washed with brine (100 ml), dried over anhydrous sodium sulfate, and concentrated in vacuo to afford a reddish oily residue. The residue was titurated in petroleum ether (100 ml) and the solvent was evaporated to give 210 g (95%) N-acetyl-D,L-phenylalanine methyl ester as a light yellow solid which could be recrystallized from diethyl ether-petroleum ether to give a colorless solid. The melting point was 62°-63° C. The proton NMR agreed with the conclusion that N-acetyl-D,L-phenylalanine methyl ester was prepared.

In a similar manner, several other examples of the present invention were carried out. The results of such experiments using varying conditions of reaction are given in the following table.

Having described the process which applicant regards as his invention, it should be recognized that changes and variations within the scope and spirit of the invention can be made by one skilled in the art and it is accordingly to be understood that the present description of the invention is illustrative only. It is desired that the invention be limited only by the lawful scope of the following claims.

I claim:

1. A process for preparing a racemic mixture of N-acyl-D,L-phenylalanine ester by reacting the azlactone of N-acyl-acetaminocinnamic acid with hydrogen at a hydrogen pressure of at least about 100 psig at a temperature within the range of from about 50°-200° C. in the presence of a nickel hydrogenation catalyst, a lower alkanol and an alkali metal or an alkaline earth metal alkoxide.

2. The process of claim 1, wherein the acyl group contains from 1-9 carbon atoms.

3. The process of claim 2, wherein the acyl group is selected from formyl, acetyl or propionyl.

4. The process of claim 1, wherein the ester group contains from 1-10 carbon atoms.

5. The process of claim 1, wherein said alkanol contains from 1 to about 10 carbon atoms.

6. The process of claim 1, wherein said alkali metal alkoxide has up to about 10 carbon atoms in the molecule.

7. The process of claim 6, wherein said alkali metal alkoxide is sodium methoxide.

8. The process of claim 1, wherein said alkaline earth metal alkoxide has up to about 10 carbon atoms in the molecule.

9. The process of claim 1, wherein said nickel hydrogenation catalyst is Raney nickel.

10. The process of claim 1, wherein the ratio of hydrogenation catalyst to azlactone is from about 3 to 100 grams of catalyst to one mole of azlactone.

11. The process of claim 1, wherein the amount of alkanol present in the reaction is an amount of from about 2 to 40 moles of alkanol per mole of azlactone.

12. The process of claim 1, wherein the alkoxide reactant is present in amounts ranging from about 0.01 to 1 mole of alkoxide per mole of azlactone.

13. A process for preparing racemic mixture of N-acetyl-D,L-phenylalanine methyl ester by reacting the azlactone of N-acetaminocinnamic acid with hydrogen at a hydrogen pressure of at least about 100 psig and at a temperature within the approximate range of 50°-200° C. in the presence of a nickel hydrogenation catalyst, methanol and sodium methoxide.

TABLE

PREPARATION OF N—ACETYL-D,L-PHENYLALANINE ESTER FROM THE AZLACTONE OF N—ACETYL-ACETAMINOCINNAMIC ACID

| Example No. | Azlactone g/mmol | | Sodium Methoxide g/mmol | | Raney Nickel g/mmol | | Methanol ml | Temp. | Reaction Time (Hours) | $H_2$ (psig) | Ester Yield % |
|---|---|---|---|---|---|---|---|---|---|---|---|
| 3 | 9.35 | 50 | 1.35 | 25 | 6 | 100 | 170 | 50° | 4.0 | 100 | 75 |
| 4 | 9.35 | 50 | 1.35 | 25 | 2.9 | 50 | 170 | 60° | 4.0 | 100 | 62 |
| 5 | 9.35 | 50 | 1.35 | 25 | 1.4 | 25 | 170 | 75° | 4.0 | 120 | >50 |
| 6 | 9.35 | 50 | 0.68 | 12 | 2.9 | 50 | 170 | 75° | 4.5 | 120 | 88 |
| 7 | 9.35 | 50 | 0.32 | 6 | 2.13 | 36 | 170 | 75° | 4.5 | 120 | 88 |
| 8 | 9.35 | 50 | 0.27 | 5 | 3.46 | 59 | 170 | 110° | 5.5 | 120 | N.R.* |
| 9 | 9.35 | 50 | 0.27 | 5 | 3.46 | 59 | 170 | 75° | 5.5 | 300 | N.R.* |
| 10 | 9.35 | 50 | 0.27 | 5 | 3.46 | 59 | 170 | 75° | 2.5 | 200 | ~100 |
| 11 | 9.35 | 50 | 0.27 | 5 | 3.46 | 59 | 170 | 75° | 2.5 | 200 | ~100 |
| 12 | 9.35 | 50 | 0.27 | 5 | 3.46 | 59 | 170 | 75° | 2.0 | 200 | ~100 |

*No reduction due to use of non-pyrophoric Raney nickel.

* * * * *